Figure 1:
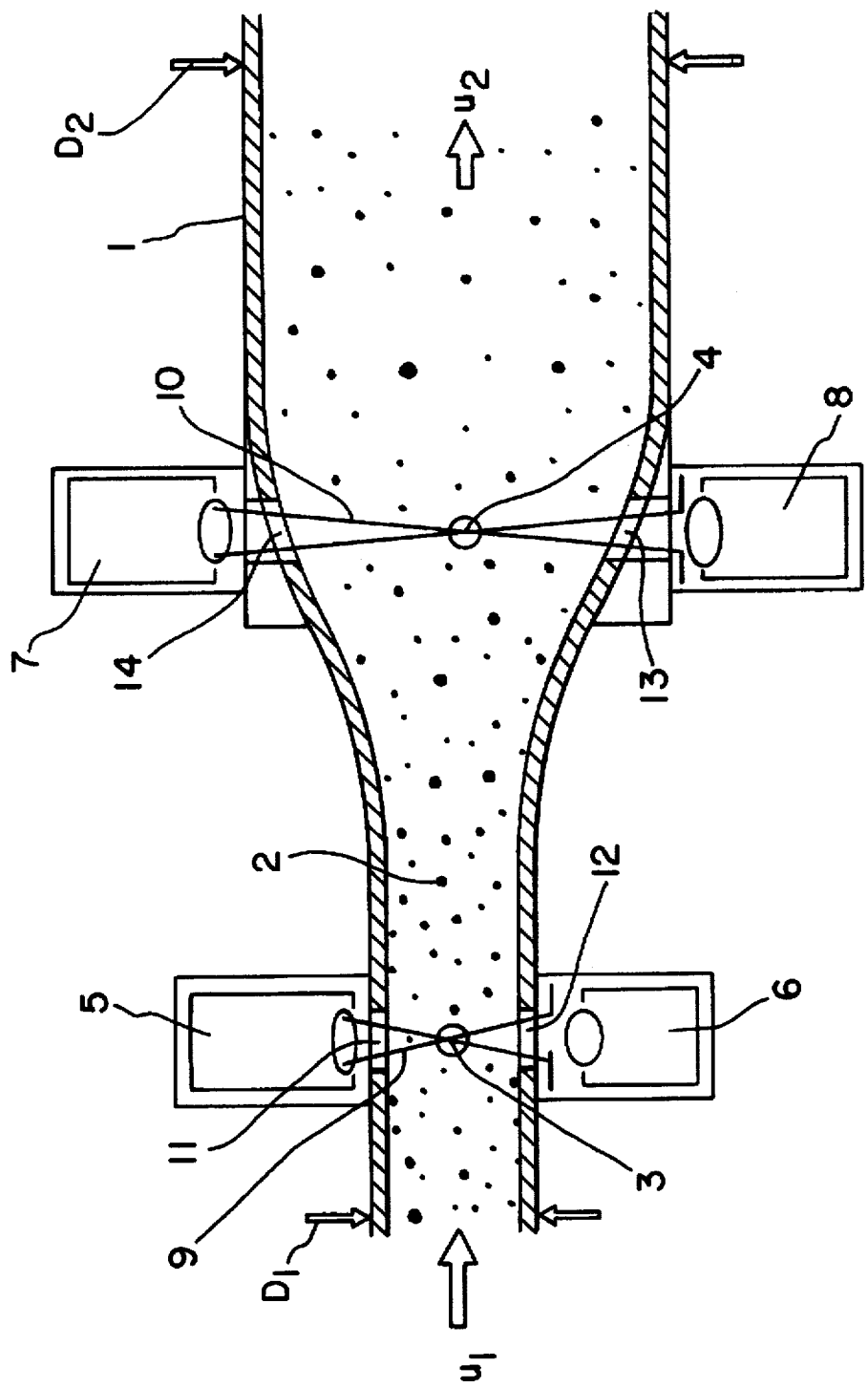

United States Patent [19]

Ruck

[11] Patent Number: 5,679,907
[45] Date of Patent: Oct. 21, 1997

[54] METHOD AND DEVICE TO DETERMINE THE AERODYNAMIC DIAMETER OF PARTICLES

[76] Inventor: Bodo Ruck, Rotenbuschle 11, D-76228 Karlsruhe, Germany

[21] Appl. No.: 409,215

[22] Filed: Mar. 23, 1995

[30] Foreign Application Priority Data

Mar. 25, 1994 [DE] Germany ............................ 44 10 422.7

[51] Int. Cl.$^6$ ................................................. G01N 15/00
[52] U.S. Cl. ........................................ 73/865.5; 73/861.41
[58] Field of Search ........................... 73/865.5, 861.05, 73/861.41, 195, 861.73; 356/335, 336

[56] References Cited

U.S. PATENT DOCUMENTS

| | | |
|---|---|---|
| 3,679,973 | 7/1972 | Smith, Jr. et al. ............... 73/865.5 |
| 3,763,428 | 10/1973 | Preist ............................ 73/865.5 |
| 4,514,257 | 4/1985 | Karlsson et al. ................ 356/335 |
| 4,529,309 | 7/1985 | Pettersson et al. .............. 356/335 |
| 5,090,233 | 2/1992 | Kogure et al. .................. 73/865.5 |
| 5,359,907 | 11/1994 | Baker et al. .................... 73/865.5 |
| 5,506,673 | 4/1996 | Kosaka et al. .................. 356/339 |
| 5,561,515 | 10/1996 | Hairston et al. ................ 356/28 |

FOREIGN PATENT DOCUMENTS 0253669   7/1987   European Pat. Off. .

OTHER PUBLICATIONS

Hirloman, E.D., 1988: "Modeling of Multiple Scattering Effects in Fraunhofer Diffraction Particle Size Analysis," Part. Part Syst. Charact., 5, 57–65.

Gréhan, G., Gouesbet, G., 1986: "Simultaneous Measurements of Velocities and Sizes of Particles in Flows Using a Combined System Incorporating a Top–Hat Beam Technique," Applied Optics, 25, 19, 3527–3538.

Jacobi, W., Eichler, J., Stolterfoht, N., 1968: "Teilchengrössgen–Spektrometrie von Aerosolen durch Lichtstreuung in einem Laserstrahl," [Particle Size Spectrometry of Aerosols by Light Diffraction in a Laser Beam], Staub–Reinhaltung Luft, 28, 8, 314–319.

Farmer, W.M., 1972: "Measurement of Particle Size, Number, Density and Velocity Using a Laser Interferometer," Journal of Applied Optics, 11, 2603–2612.

Adrian, R.J., Orloff, K.L., 1977: "Laser Anemometer Signals: Visibility Characteristics and Application to Particle Sizing", Applied Optics, 16, 3, 677–684.

Bachalo, W.D., Houser, M.J., 1984: "Phase/Doppler Spray Analyzer for Simultaneous Measurements of Drop Size and Velocity Distributions", Optical Engineering, 23, 5, 583–590.

(List continued on next page.)

Primary Examiner—Richard Chilcot
Assistant Examiner—Max H. Noori
Attorney, Agent, or Firm—Baker & Daniels

[57] ABSTRACT

The invention concerns a method and device for determining the aerodynamic diameter of particles carried in a flow. To that end, the velocity of the flow is altered in an area and the particle velocity measured at at least one point before said area and at at least one point in or after said area. Owing to the alteration of the flow velocity, the particles carried in the flow are with increasing aerodynamic diameter retarded or accelerated increasingly more slowly than the carrier fluid, depending on whether an area of flow retardation or flow acceleration is concerned. Knowing the constraints makes it possible, therefore, by measuring the particle velocity in or shortly after this area of altered flow velocity, to infer the aerodynamic diameter. Correlating the particle velocity data thus obtained with the as well performed particle velocity measurement before the area of flow velocity alteration, where all of the particles of different size still have approximately the same velocity, allows determining the aerodynamic diameter independently of the inflow velocity of the particle-laden flow. Hence, a device basing on the method can be installed directly in a technical circulation, which enables "in-situ" measurements of the aerodynamic diameter of particles.

12 Claims, 2 Drawing Sheets

OTHER PUBLICATIONS

Saffmann, M., 1989: "Phasen Doppler Methode' zur optischen Partikelgrößerunessung," [Phase Doppler Method for Optical Particle Size Measurement], Technisches Messen tm, 56, 7/8, 298–303.

Bauckhage, K., Schulte, G., 1990: "Phasen–Doppler–Anemometrie," in Lasermethoden in der Strömungsmesstechnik, B. Ruck (Publ.), AT–Fachverlag Stuttgart, 7, 263–282, ISBN: 3–921 681–01–4.

Adnan, Al–aithawi, Kornis, J., Fuzessy, Z., 1990: "Fully Automatic System to Evaluate a Particle Size Hologram," Proc. 2nd Int. Congress on Optical Particle Sizing, Arizona State University, Tempe, 556–564.

Yeh, C.–N., Kosaka, H., Kamimoto, T., 1993: "A Fluorescence/Scattering Imaging Technique for Instantaneous 2–D Measurement of Particle Size Distribution in a Transient Spray," Proc. 3rd Int. Congress on Optical Particle Sizing, Yokohama, Japan, 355–361.

Gougeon, P., Le Toulouzan, J.N., Gouesbet, G., Thénard, C., 1987: "Optical Measurements of Particle Size and Concentration in Densely Laden Media Using a Visible/Infrared Double Extinction Technique," J. Phys. E: Sci. Instr., 20, 1235–1242.

Durst, F., 1982: "Review—Combined Measurements of Particle Velocities, Size Distributions, and Concentrations," Journal of Fluids Engineering, 104, 284–295.

Gouesbet, G., 1985: "A Review on Measurements of Particle Velocities and Diameters by Laser Techniques, with Emphasis on Thermal Plasmas," Plasma Chemistry and Plasma Processing, 5, 2, 91–117.

Tayali, N.E., Bates, C.J., 1990: "Particle Sizing Techniques in Multiphase Flows: A Review," Flow Meas. Instrum., vol. 1, Jan. 1990, 77–105.

Wilson, J.C., Liu. B.Y.H., 1980: "Aerodynamic Particle Size Measurement by Laser–Doppler Velocimetry," J. Aerosol Sci., vol. 11, 2, 139–150.

Kirsch, K.J., Mazumder, M.K., 1975: "Aerosol Size Spectrum Analysis Using Relaxation Time Measurements", 11 Applied Physics Letters, 26, 4, 193–195.

Mazumder, M.K., Kirsch, K.J., 1977: "Single Particle Aerodynamic Relaxation Time Analyzer for Particle Size Measurements", Rev. Sci. Instrum., vol. 48, 6, 622–624.

Renninger, R.C., Mazumder, M.K., Testerman, M.K., 1981: "Particle Sizing by Electrical Single Particle Aerodynamic Relaxation Time Analyzer," Rev. Sci. Instrum., 52(2), 242–246.

METHOD AND DEVICE TO DETERMINE THE AERODYNAMIC DIAMETER OF PARTICLES

The invention concerns a method and a device for determining the aerodynamic diameter of particles carried in a flow. The aerodynamic diameter is known also as aerodynamic equivalent diameter of a spherical particle with a specific standard density, which particle displays experimentally an aerodynamic behavior the same as the real particle. In the invention it is irrelevant whether aerosols or other solid or liquid particles in gases or liquids are concerned. Conceivable are minutest particles in gas or liquid flows that possess diameters down to the micrometer range.

Methods and devices for particle diameter determination are used notably in particle metrology. Today, the measurement of particle diameters, and thus particle size distributions, is an important prerequisite for the technological advancement, for instance in production engineering. Examples are methods of spray cooling, atomization, coating, processing of mixtures or enameling. Comparable notions apply to the area of clean-room technology or environmental protection, where the detection of airborne substances and the measurement of corresponding particle size distribution have attained central significance in analytics.

Existing particle size measuring methods allow a rough classification in mechanical filter and inertial separators, electrical measuring methods, radioactive measuring methods and optical measuring methods, a further subdivision being whether assessments are carried out on the individual particle or on particles collectively. Common to most non-optical measuring methods is that either an "in-situ" determination of the particle size distribution is not possible, since elaborate evaluations, for example of impactor or filter surfaces, must be carried out first, or the measuring methods themselves affect the measuring results, as for instance with charge-based particle size measuring methods. These are contrasted by the optical or laser-optical measuring methods. Particular emphasis attaches here to the measuring methods that allow "in-situ" particle diameter measurement, to the class of which pertains the present invention.

The optical particle size measuring methods developed in the last two decades employ predominantly laser light. The laser light is here mostly focussed in a point, the so-called measuring volume, through which the particles being analyzed are passed [1,2]. The scatter light produced by particles passing through this measuring volume is evaluated in view of various properties. For example, there are measuring systems used which base on the diffraction of the incident laser radiation on the particles [3]. Utilized here is the Fraunhofer diffraction, and propositions on the geometric diameter of particles become possible. Other systems evaluate the amplitude level of the light scattered on the particles [4,5] to infer the particle size, which corresponds to determining an optical equivalent diameter. Still other measuring methods allow conclusions to the particle size [6,7] based on the modulation depth of laser-doppler anemometry signals (LDA). As a more novel measuring method, the phase doppler anemometry (PDA) has established itself, where LDA signals are received with two spatially separated photodetectors and the particle size is inferred [8-10] from the time offset (phase delay) of the signals. The PDA technique provides a geometric equivalent radius. Concluding mention is made yet of holographical methods for particle size determination [11] as well as of methods which base on effects of fluorescence [12] and turbidation [13]. In the past, however, these methods have been unable to attain any practical relevance, since either their relatively complicated handling prohibits "in-situ" measurements or their informational indistinctness is to be judged as being excessive. Summary illustrations and explanations on optical and laser-optical measuring methods for particle size measurement are contained in the literature in the form of overview articles [14-16].

In both our technical and natural environment it matters frequently to determine the aerodynamic diameter of particles. Meant thereby is the diameter of a spherical particle with a defined specific gravity, which in the flow displays aerodynamically the same behavior as the real particle of possibly complex shape. Decisive significance attaches to the aerodynamic diameter in terms of the propagation of pollutants, deposition of particles, optimization of technical particle-specific processes, or also in medicine, for estimating the respirability of aerosols.

Therefore, the problem underlying the invention is determining the aerodynamic diameter of particles and to enable the assessment of the aerodynamic particle size distribution.

This problem is solved by a method with the features set forth in claim 1, or by a device with the features in claim 4. Favorable embodiments and developments derive from the subclaims.

Characteristic for the method is that the velocity of the particle-laden flow is altered in an area and particle velocity measurements are carried out at at least one point before said area and at at least one point in or after that area. Altering the flow velocity in a closed conduit is effected preferably by altering its cross section. Alteration of the cross section creates areas of either retardation or acceleration of flow. Comparable areas can be obtained also in an open flow, for instance in the circumfluence of an obstacle.

Characteristic for the method is that the particle velocities are measured at at least two points in the field of flow, with one measuring point contained in the undisturbed inflow, in which all of the particles still have approximately the same velocity. The second measuring point is located in or after the area of flow velocity alteration. The particle velocity measurements can be carried out by two measuring systems or also by only one that is mobile and accesses the two mentioned measuring points in short succession. Owing to the different following capacity of particles in zones of flow retardation or flow acceleration, thus in zones with existing velocity gradients, different particle velocities are measured in these zones, and shortly thereafter still, depending on the aerodynamic diameter of the particles. With a constant entering velocity of the particles, for example in a conduit according to the present invention, individual velocities characteristic for each particle are measured at a second point, which relate directly to the aerodynamic diameter of the particle. Since the entering velocity of the particles is measured at the first measuring location, particle velocity and particle size can be coordinated clearly, even when the entering velocity of the particles is no longer constant, which is frequently the case in ongoing technical flow processes. The aerodynamic particle size distributions can then be obtained from a statistical evaluation of the individual aerodynamic diameters. The calibration of the inventional measuring method can be carried out experimentally or, in a simpler manner, theoretically, since the motion equation for spherical particles in a viscous fluid is known.

Methods approximating the present invention, but without possessing its decisive characterizing features, are contained in the relevant data banks [17-21]. In [17], a particle-laden air flow is at constant velocity forced through a nozzle. The velocity of the particles is measured directly after the nozzle, by means of a laser-optical particle velocity measuring method. Large particles are unable to follow the acceleration of flow in the nozzle quickly and, therefore, return a lower velocity. Characteristic for the method according to [17] is that the particle velocity is measured only at one point after an acceleration of flow and that the particle-laden inflow must have a constant velocity, which can be accomplished only with considerable experimental expense. The method operates similar to sampling, for instance from the flow space. Viewed as a further disadvantage with this method should be that shear forces cause a tear-up of larger particles as they pass through the nozzle, which may adulterate the resulting determination of the aerodynamic diameter.

The utilization of inertial effects underlies also the method according to [18], where the flow laden with particles is directed at a hemispherical obstacle, causing a deceleration of the carrier fluid to a value of zero at the point of stagnation. Particles of different size join in the deceleration only in a manner characteristic for their aerodynamic diameter, so that different particle velocities are being measured at a point spaced a certain distance before the stagnation point. The method resembles greatly the one illustrated before, according to [17], since it represents a single-point measurement. To avoid equivocities, it requires keeping the velocity of the inflow constant in the measurement and that it be known a priori. For when altering the velocity of the inflow, it will no longer be possible to recognize whether the particle velocities measured shortly before the point of stagnation result now from a different aerodynamic particle diameter or from altering the velocity of the inflow. Such equivocacy is associated with most of the single-point measuring methods and precludes their application under realistic, variable conditions of flow.

The inertia of larger particles is utilized also in [19,20], where a particle-laden flow is passed across a source of sound and the entrained particles are thereby accelerated transverse to the direction of flow. The transverse velocity is measured with the laser-doppler anemometer and serves as a measure for the particle size. Another paper [21] bases on the electrical charging of particles and the subsequent effect of an alternating field. Information on the aerodynamic diameter of the particles can be derived from the phase delay which the particles display as compared to the phase of the alternating field. Common to all of these methods is also that measurements are carried out at one point only and, in the interest of clarity of the measuring data, constant constraints, or conditions of inflow, must be established. Additionally, e.g., electrical charging techniques are being used which, as we know today, affect the particle phase.

All this is contrasted by the present invention, which by an at least twofold particle velocity measurement enables the determination of the aerodynamic diameter, independently of the inflow velocity of the particle-laden flow. A sampling of the particle-laden fluid becomes dispensable. A device based on the method can thus be operated for direct "in-situ" determination of the aerodynamic diameter of particles in open or enclosed circulations with different, that is, varying flow velocities. Such particle-laden circulations are technically of high practical relevance, for instance in power-generating, power-consuming and fluidics machines, in process engineering, material processing, spraying and atomizing techniques, coating techniques, clean-room techniques etc. In the inventional measuring method, the particles being measured are exposed to only minimal shear stress, for instance due to a fluidically favorable shaping of the conduit. An adulteration of the results obtained in determining the aerodynamic diameter of particles, due to shear processes, is thus extensively avoided. This fact is particularly important for practical application, where highly precise inferences to the volume and mass concentration are frequently required. The inventional method enables a noncontact, nonimpairing determination of the aerodynamic diameter of particles, for instance with the use of optical particle velocity measuring systems based on diode lasers and thereof the arrival at the particle size distribution. A further advantage of the inventional method is constituted in that the particle size determination, complex as such, is being reduced to the very well manageable particle velocity measurement, for which a great many electronic evaluation options are available. Therefore, the measurement of the aerodynamic diameter of particles, owing to the inventional method, can in the future doubtless be carried out in a distinctly more low-cost and speedier fashion.

Further advantages and characteristics of the invention derive from the claims and the following specification, which illustrates an embodiment of the invention and the qualitative pattern of the velocity of particles in passing through an inventional device in greater detail with the aid of two drawings.

Figure 2:
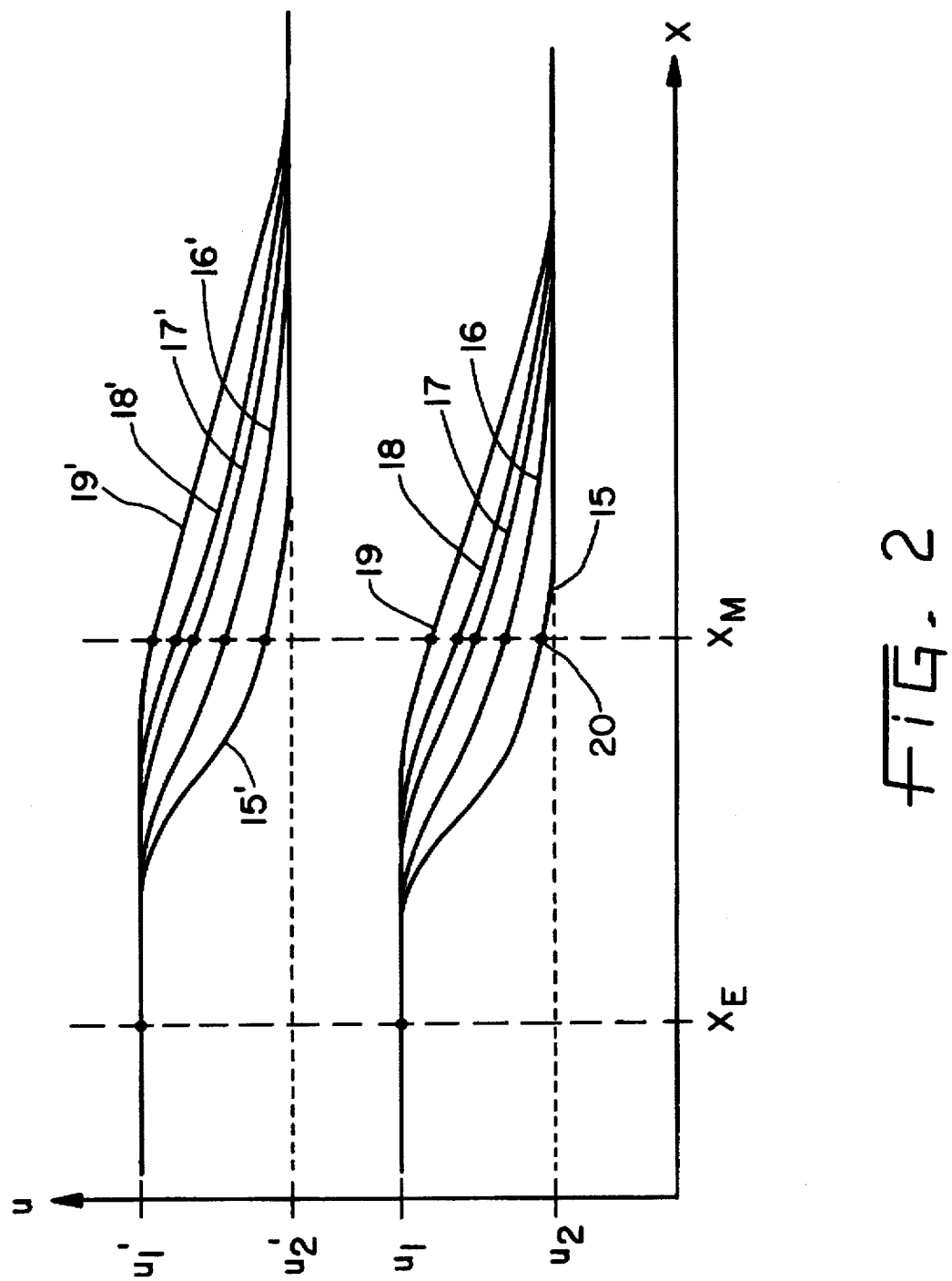

FIG. 1 shows an embodiment of the invention based on a conduit with flow retardation and with two laser-doppler anemometry measuring systems for particle velocity measurement;

FIG. 2, the qualitative pattern of particle velocities as a function of an embodiment basing on a conduit with flow retardation.

As illustrated in FIG. 1, the invention can be reduced to practice, e.g., by means of a circular tube section 1 whose cross section expands from a diameter $D_1$ to a diameter $D_2$. The transition from diameter $D_1$ to a larger diameter $D_2$ may be continuous or abrupt. A flow laden with particles 2 passing through this fluidics assembly is abruptly retarded by its cross-sectional expansion. With increasing aerodynamic particle size, the entrained particles 2 are being retarded increasingly more slowly. When now measuring, through a window 13, 14, the velocity of the particles in or shortly after the area of cross-sectional expansion, at a point 4, with the aid of a laser-optical particle velocity measuring system comprised of a laser-doppler anemometer (LDA) with transmitter 7 and receiver 8 and laser beams 10 directed at the measuring point, different velocities are found for particles with different sizes. Using a second LDA particle velocity measuring system, consisting of transmitter 5 and receiver 6 and pertaining laser beams 9 directed at the measuring point, the entering velocity of the particles is measured, through the window 11, 12, at a point 3 before the cross-sectional expansion, where the particles differing in size still have approximately the same velocity. The aerodynamic particle diameter can be found, independently of the flow velocity at the entrance, by relating the velocities measured individually for each particle at point 4 to the entering velocity at point 3. The physical procedure on which the measuring method is based allows also theoretical explanation. Decisive parameters in this case are the entering velocity $u_1$, the viscosity of the fluid, the ratio of cross-sectional surfaces after and before the alteration of cross section, as well as the particle size and density of the particle material, which in calculating the aerodynamic equivalent diameter of a spherical particle are frequently assumed to have a standard density of 1 g/cm$^3$.

In a manner corresponding to the embodiment illustrated in FIG. 1, FIG. 2 depicts the qualitative pattern of the velocities for particles with differing aerodynamic diameters. The velocity curves 15 through 19 represent here in ascending order particles with incrementing aerodynamic diameters, which enter the measuring conduit at an entering velocity $u_1$ that is measured at the location $x_E$ before the alteration of the cross section and corresponds to point 3 in FIG. 1. By measuring at point $X_M$, which corresponds to the second measuring point 4 in FIG. 1, yields for each aerodynamic particle diameter a characteristic particle velocity value; refer to 20, for example. After a sufficiently long travel and time, the particle velocities adapt then again to the altered fluid velocity $u_2$. If the entering velocity $u_1$ changes to a new value $u_1'$, unequivocal particle velocity values are measured as well for particles with incrementing aerodynamic diameter, represented by the velocity curves 15' through 19' in ascending order, which velocity values adapt over time to the altered fluid velocity $u_2'$. The aerodynamic diameter can be instantaneously determined mathematically by way of a computer or by means of a calibration curve established with calibration particles, from the velocity values measured at points $x_E$ and $x_M$. A prerequisite for the "in-situ" reliability of the method, with variable flow velocities, is thus that the entering velocity be measured as a characteristic parameter for identification of the group of curves and that it be available. Exactly the latter is a characteristic feature of the present invention.

BIBLIOGRAPHY

[1] Ruck, B. (Publisher), 1990: "Lasermethoden in der Strömungsmeßtechnik" [Laser Methods in Fluidics Metrology], techn. book, AT-Fachverlag, Stuttgart, 3, 99–150, ISBN: 3-921 681-01-4

[2] Ruck, B., 1981: "Untersuchungen zur optischen Messung von Teilchengröße und Teilchengeschwindigkeit mit Streulichtmethoden," [Studies on the Measurement of Particle Size and Particle Velocity Using Scattered Light Methods], Dissertation, Karlsruhe University

[3] Hirleman, E. D., 1988: "Modeling of Multiple Scattering Effects in Fraunhofer Diffraction Particle Size Analysis," Part. Part Syst. Charact., 5, 57–65

[4] Gréhan, G., Gouesbet, G., 1986: "Simultaneous Measurements of Velocities and Sizes of Particles in Flows Using a Combined System Incorporating a Top-Hat Beam Technique," Applied Optics, 25, 19, 3527–3538

[5] Jacobi, W., Eichler, J., Stolterfoht, N., 1968: TeilchengrößenSpektrometrie von Aerosolen durch Lichtstreuung in einem Laserstrahl," [Particle Size Spectrometry of Aerosols by Light Diffraction in a Laser Beam], Staub—Reinhaltung Luft, 28, 8, 314–319.

[6] Farmer, W. M., 1972: "Measurement of Particle Size, Number, Density and Velocity Using a Laser Interferometer," Journal of Applied Optics, 11, 2603–2612.

[7] Adrian, R. J., Orloff, K. L., 1977: Laser Anemometer Signals: Visibility Characteristics and Application to Particle Sizing," Appl. Opt., 16, 3, 677–684.

[8] Bachalo, W. D., Houser, M. J. 1984: "Phase/Doppler Spray Analyzer for Simultaneous Measurements of Drop Size and Velocity Distributions," Optical Engineering, 23, 5, 583–590.

[9] Saffmann, M., 1989: Phasen-Doppler-Methode zur optischen Partikel-größenmessung,"[Phase Doppler Method for Optical Particle Size Measurement], tm Technisches Messen, 56, 7/8, 298–303.

[10] Bauckhage, K., Schulte, G., 1990: "Phasen-Doppler-Anemometrie," in Lasermethoden in der Strömungsmeßtechnik, B. Ruck (Publ.), AT-Fachverlag Stuttgart, 7, 263–282, ISBN: 3-921 681-01-4

[11] Adnan, Al-aithawi, Kornis, J., Fuzessy, Z., 1990: "Fully Automatic System to Evaluate a Particle Size Hologram." Proc. 2nd Int. Congress on Optical Particle Sizing, Arizona State University, Tempe, 556–564

[12] Yeh, C. -H., Kosaka, H., Kamimoto, T., 1993: "A Fluorescence/Scattering Imaging Technique for Instantaneous 2-D Measurement of Particle Size Distribution in a Transient Spray," Proc. 3rd Int. Congress on Optical Particle Sizing, Yokohama, Japan, 355–361.

[13] Gougeon, P., Le Toulouzan, J. N., Gouesbet, G., Thénard, C., 1987: "Optical Measurements of Particle Size and Concentration in Densely Laden Media Using a Visible/Infrared Double Extinction Technique," J. Phys. E: Sci. Instr., 20, 1235–1242

[14] Durst, F., 1982: "Review—Combined Measurements of Particle Velocities, Size Distributions, and Concentrations," J. of Fluids Engineering, 104, 284–295

[15] Gouesbet, G., 1985: "A Review on Measurements of Particle Velocities and Diameters by Laser Techniques, with Emphasis on Thermal Plasmas," Plasma Chemistry and Plasma Processing, 5, 2, 91–117

[16] Tayali, N. E., Bates, C. J., 1990: "Particle sizing techniques in multiphase flows: A review,"Flow Meas. Instrum., Vol. 1, January 1990, 77–105

[17] Wilson, J. C., Liu. B. Y. H., 1980: "Aerodynamic Particle Size Measurement by Laser-Doppler Velocimetry,"J. Aerosol Sci., 11, 2, 139–150

[18] Clift, R., Seville, J. P. K., Tate, A. H. J./National Research Development Corporation, 1987: Method and apparatus for the measurement of the size of particles entrained in a gas," European Patent Application, publication number EP 0 253 669 A2, European Patent Office

[19] Kirsch, K. J., Mazumder, M. K., 1975: "Aerosol Size Spectrum Analysis Using Relaxation Time Measurements," Applied Physics Letters, 26, 4, 193–195

[20] Mazumder, M. K., Kirsch, K. J., 1977): "Single Particle Aerodynamic Relaxation Time Analyzer for Particle Size Measurements," Rev. Sci. Instrum., 48, 6, 622–624

[21] Renninger, R. G., Mazumder, M. K., Testerman, M. K., 1981: "Particle Sizing by Electrical Single Particle Aerodynamic Relaxation Time Analyzer," Rev. Sci. Instrum., 52, 2, 242–246

I claim:

1. Method for determining the aerodynamic diameter of particles carried in a flow, comprising the steps of:

altering the flow velocity of the particles in an area;

measuring a first particle velocity at at least one point in or after said area;

measuring a second particle velocity at a point before said area; and determining the aerodynamic diameter of particles based on the first and second measured particle velocities.

2. Method according to claim 1, wherein said method is carried out "in-situ."

3. Method according to claim 1, wherein said altering step comprises passing the flow through a closed conduit and altering the velocity of the flow by altering the cross section of the conduit.

4. Device for determining the aerodynamic diameter of particles carried in a flow, comprising:

a conduit having a design that changes the flow velocity, said conduit having a first area associated with a first particle velocity and a second area associated with a second particle velocity; and a measuring system capable of measuring particle velocities at at least two points in the field of flow, one of said two points disposed in said first area, another of said two points disposed in said second area.

5. Device according to claim 4, wherein said conduit includes two different cross sections.

6. Device according to claim 4, wherein said conduit includes an open flow area with areas of one of flow retardation and flow acceleration.

7. Method according to claim 1, wherein said measuring steps comprise measuring the particle velocity using one of optical and laser-optical metrology methods.

8. Method according to claim 7, wherein said measuring steps comprise measuring particle velocity by one of laser-doppler anemometry and laser dual-focus anemometry.

9. Method according to claim 7, wherein said measuring steps comprise measuring particle velocity using light beam measuring methods.

10. Device according to claim 4, wherein said measuring system uses optical or laser-optical metrology methods.

11. Device according to claim 10, wherein said measuring system uses one of laser-doppler anemometry and laser dual-focus anemometry methods.

12. Device according to claim 11, wherein said measuring system uses light beam measuring methods.

* * * * *